(12) United States Patent
Govari (10) Patent No.: US 7,090,639 B2
(45) Date of Patent: Aug. 15, 2006

(54) ULTRASOUND CATHETER CALIBRATION SYSTEM

(75) Inventor: Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 449 days.

(21) Appl. No.: 10/447,940

(22) Filed: May 29, 2003

(65) Prior Publication Data

US 2004/0254458 A1    Dec. 16, 2004

(51) Int. Cl.
*A61B 8/00* (2006.01)
(52) U.S. Cl. .................................. 600/437; 73/1.82
(58) Field of Classification Search ................ 600/437, 600/443, 459, 466–7; 73/1.79, 1.82, 1.86; 310/334; 128/899
See application file for complete search history.

(56) References Cited

U.S. PATENT DOCUMENTS

| | | | |
|---|---|---|---|
| 3,644,825 A | 2/1972 | Davis, Jr. et al. | |
| 3,868,565 A | 2/1975 | Kuipers | |
| 4,017,858 A | 4/1977 | Kuipers | |
| 4,054,881 A | 10/1977 | Raab | |
| 4,284,950 A * | 8/1981 | Burl et al. | 324/320 |
| 4,567,896 A | 2/1986 | Barnea et al. | |
| 4,849,692 A | 7/1989 | Blood | |
| 5,042,486 A | 8/1991 | Pfeiler et al. | |
| 5,391,199 A | 2/1995 | Ben-Haim | |
| 5,558,091 A | 9/1996 | Acler et al. | |
| 5,752,513 A | 5/1998 | Acker et al. | |
| 5,833,608 A | 11/1998 | Acker | |
| 5,913,820 A | 6/1999 | Bladen et al. | |
| 6,112,113 A | 8/2000 | Van Der Brug et al. | |
| 6,138,495 A | 10/2000 | Paltieli et al. | |
| 6,161,032 A * | 12/2000 | Acker | 600/424 |
| 6,216,029 B1 | 4/2001 | Paltieli | |
| 6,248,083 B1 | 6/2001 | Smith et al. | |
| 6,266,551 B1 * | 7/2001 | Osadchy et al. | 600/424 |
| 6,335,617 B1 * | 1/2002 | Osadchy et al. | 324/202 |
| 6,347,460 B1 * | 2/2002 | Forrer et al. | 33/626 |
| 6,366,799 B1 * | 4/2002 | Acker et al. | 600/424 |
| 6,370,411 B1 * | 4/2002 | Osadchy et al. | 600/372 |
| 6,453,190 B1 * | 9/2002 | Acker et al. | 600/424 |
| 6,484,118 B1 * | 11/2002 | Govari | 702/150 |
| 6,545,468 B1 * | 4/2003 | Kuo et al. | 324/226 |
| 6,604,404 B1 * | 8/2003 | Paltieli et al. | 73/1.82 |
| 6,775,404 B1 * | 8/2004 | Pagoulatos et al. | 382/154 |
| 6,792,370 B1 * | 9/2004 | Satoh et al. | 702/95 |
| 2004/0039285 A1 * | 2/2004 | Ustuner et al. | 600/459 |

FOREIGN PATENT DOCUMENTS

| | | |
|---|---|---|
| EP | 0 776 176 B1 | 4/1997 |
| FR | 763861 | 5/1934 |
| WO | WO 99/27837 A2 | 6/1999 |
| WO | WO 01/01845 A2 | 1/2001 |

OTHER PUBLICATIONS

European Search Report EP04253230 dated Sep. 8, 2004.

* cited by examiner

*Primary Examiner*—Francis J. Jaworski
(74) *Attorney, Agent, or Firm*—Louis J. Capezzuto (57) ABSTRACT

Apparatus is provided for calibrating a probe having a position sensor and an ultrasonic transducer. The apparatus includes a test fixture, which includes an ultrasonic target disposed therein at a known position. A computer is adapted to receive a position signal generated by the position sensor while the transducer is in alignment with the ultrasonic target, determine an orientation of the probe in a frame of reference of the test fixture, and determine calibration data for the probe responsive to the orientation of the probe.

51 Claims, 4 Drawing Sheets

ULTRASOUND CATHETER CALIBRATION SYSTEM

FIELD OF THE INVENTION

The present invention relates generally to systems for medical diagnosis and treatment, and specifically to medical catheters whose location can be detected.

BACKGROUND OF THE INVENTION

Various methods and devices have been described for determining the position of a probe or catheter tip inside the body using electromagnetic fields, such as in U.S. Pat. No. 5,391,199 to Ben-Haim, European Patent 0 776 176 to Ben-Haim et al., U.S. Pat. Nos. 5,833,608 and 6,161,032 to Acker, and U.S. Pat. Nos. 5,558,091 and 5,752,513 to Acker et al., all of which are assigned to the assignee of the present patent application and are incorporated herein by reference. U.S. Pat. No. 5,913,820 to Bladen et al. and U.S. Pat. No. 5,042,486 to Pfeiler et al., both of which are incorporated herein by reference, also describe electromagnetic position-determination systems. Other electromagnetic tracking systems, not necessarily for medical applications, are described in U.S. Pat. No. 3,644,825 to Davis, Jr. et al., U.S. Pat. Nos. 3,868,565 and 4,017,858 to Kuipers, U.S. Pat. No. 4,054,881 to Raab, and U.S. Pat. No. 4,849,692 to Blood, which are likewise incorporated herein by reference.

Because of manufacturing variations, the coils generally used in the position sensors of these position-determining systems to generate position signals may not be precisely oriented with the body of the probe. Additionally, the distance of the coils from the tip of the probe may not be precisely known, and there may be slight variations in the relative gains of the coils in response to externally-applied fields. U.S. Pat. No. 6,266,551 to Osadchy et al., which is assigned to the assignee of the present patent application and is incorporated herein by reference, describes methods and apparatus for pre-calibrating a probe, preferably at the time of manufacture, so as to measure and compensate for variations in the positions, orientations and gains of the coils. To calibrate the probe, a mechanical jig holds the probe in one or more predetermined positions and orientations, and radiators generate known, substantially uniform magnetic fields in the vicinity of the jig. Signals generated by the coils are analyzed and used to produce calibration data regarding the gains of the coils and deviations of the coils from orthogonality.

Various methods and devices have been described for storing, in a probe, information specific to the probe, such as calibration and identification information. These devices generally include a microchip incorporated in the probe. For example, the above-cited U.S. Pat. No. 6,266,551 to Osadchy et al. describes the incorporation of an electronic microcircuit in a probe, which stores information relating to calibration of the probe. Such information can include an encrypted calibration code and/or a usage code, which controls availability of the probe to a user thereof.

U.S. Pat. No. 6,370,411 to Osadchy et al., which is assigned to the assignee of the present patent application and is incorporated herein by reference, describes a catheter assembly comprising a catheter of minimal complexity and a connection cable which connects the proximal end of the catheter to a console. The catheter comprises a microcircuit which carries substantially only information specific to the catheter, such as calibration data, which is not in common with other catheters of the same model. The cable comprises an access circuit which receives the information from the catheter and passes it in a suitable form to the console.

U.S. Pat. No. 6,248,083 to Smith et al., which is incorporated herein by reference, describes a guide wire assembly having a measuring device mounted in the distal end portion thereof. It also has an interface cable which includes information storage, containing calibration/temperature compensation data, uniquely characteristic of the measuring device. The calibration data is used with uncompensated output from the measuring device to calculate a correct measurement value.

U.S. Pat. No. 6,112,113 to Van Der Brug et al., which is incorporated herein by reference, describes an image-guided surgery system that includes a position measuring system for measuring a position of an instrument. The image-guided surgery system includes a test system which is arranged to measure the instrument, using the position measuring system, by measuring a calibration position of a reference part of the instrument while an object part of the instrument is situated in a calibration location or in a test position.

U.S. Pat. No. 6,335,617 to Osadchy et al., which is assigned to the assignee of the present patent application and is incorporated herein by reference, describes a method for calibrating a magnetic field generator. According to the method, magnetic field sensors are affixed to a probe in known positions and orientations, and one or more known locations in the vicinity of the magnetic field generator are selected. The magnetic field generator is driven so as to generate a magnetic field. The probe is moved in a predetermined, known orientation to each of the locations, and signals are received from the sensors at each of the locations. The signals are processed to measure the amplitude and direction of the magnetic field, at the respective positions of the sensors, and to determine calibration factors relating to the amplitude and direction of the magnetic field in the vicinity of the magnetic field generator.

U.S. Pat. No. 4,567,896 to Barnea et al., which is incorporated herein by reference, describes a sector-scan ultrasonic imaging apparatus having a biopsy attachment for positioning a biopsy needle relative to the ultrasonic scan head of the imaging apparatus. The biopsy needle is calibrated with a scan head coordinate system which defines a sector sweep of the scan head by determining the coordinates of the needle in the scan head coordinate system independently of determining the particular spatial relationship of the needle in operative position relative to the scan head. A calibration member adapted to be mounted on the biopsy attachment includes at least two ultrasonic reflection regions which are scanned by the scan head during the calibration mode and displayed on an image display device. The display of these reflection regions enables the needle coordinates to be determined using the predetermined geometric relationship of the calibration member with respect to the imaging apparatus housing.

SUMMARY OF THE INVENTION

It is an object of some aspects of the present invention to provide apparatus and methods for calibrating an ultrasound transducer with respect to a position sensor and a catheter.

It is also an object of some aspects of the present invention to provide apparatus and methods that increase the accuracy of procedures performed with a catheter comprising a position sensor and an ultrasound transducer.

It is a further object of some aspects of the present invention to provide apparatus and methods that increase the accuracy of the determination of positions and orientations of structures imaged within the body using an ultrasound transducer affixed to a catheter.

It is yet a further object of some aspects of the present invention to provide apparatus and methods for convenient electronic storage and recall of calibration information regarding a catheter.

In preferred embodiments of the present invention, a catheter system comprising a catheter for insertion into the human body is provided. The catheter comprises a position sensing device, which typically comprises three non-concentric coils, and an ultrasound transducer, which is typically used for ultrasound imaging within a patient. A test fixture, such as a jig, preferably comprising three mutually-orthogonal pairs of parallel radiator coils, mounted on a base, is used first to calibrate the gains of the coils and then to calibrate the respective angular orientations of the coils relative to the catheter, so as to correct for deviations from orthogonality. These steps are preferably performed by using apparatus and methods described in the above-cited U.S. Pat. No. 6,266,551 to Osadchy et al. The jig is further used to calibrate the angular orientation of the ultrasound transducer relative to the position sensing device and to the catheter. For this calibration, the ultrasound transducer emits ultrasonic radiation and receives the radiation reflected back from a target disposed in a known, fixed location in the jig. The angular orientation of the distal end of the catheter is varied until radiation reflected back from the target is centered with respect to the ultrasound transducer, at which point the angular orientation of the distal end of the catheter with respect to the target is measured using the position sensing device. Based on this orientation, the orientation of the ultrasound transducer with respect to the position sensing device and the catheter is calculated.

Advantageously, this calibration enables the precise registration between the ultrasound images captures by the catheter during a medical procedure and the fixed, external frame of reference in which the catheter coordinates are determined. As a result, embodiments of the present invention allow the positions and orientations of structures imaged within the body to be determined with high accuracy. In embodiments of the present invention, the orientation of the ultrasound transducer with respect to the catheter is typically calibrated to within 0.1 degrees. As a result, the position of a reconstructed pixel in an ultrasound image of a structure 5–7 centimeters away from the ultrasound transducer can be determined to within one millimeter, which represents a high level of precision.

Preferably, the jig further comprises a catheter clamp assembly. The clamp assembly comprises a clamp base, which comprises a universal joint that is able to pivot on the rotational axes of pitch and yaw with respect to the long axis of the catheter. The universal joint is fixed to one or more of the jig's radiator coils in a known position and orientation. The jig further comprises an ultrasound target of known geometry, size, and material, fixed in a known position. The target, for example, may comprise a small "bubble" made of ultrasound-reflecting material.

The catheter is typically inserted in a groove of the clamp assembly with the distal end of the catheter pointing in the direction of the target, such that the distal end protrudes from the groove by a predetermined distance. The catheter is rotated about its long axis to a desired rotational orientation.

For some applications, the displacements of the coils relative to the catheter tip are calibrated. This is preferably performed by using a jig (not shown) and methods for this purpose, such as those described in the above-cited U.S. Pat. No. 6,266,551 to Osadchy et al.

In some preferred embodiments of the present invention, the calibration correction that is determined in accordance with the methods described above is thereafter stored electronically in a memory device, which is preferably incorporated in the catheter. When the catheter is coupled to a console for use during a medical procedure, this memory device is accessible to a computer in the console. Apparatus and methods for such a memory device described in the above-cited U.S. Pat. No. 6,266,551 to Osadchy et al. may be used, or, alternatively, other apparatus and methods known in the art may be used.

There is therefore provided, in accordance with an embodiment of the present invention, a method for calibration, including:

placing a probe that includes a position sensor and an ultrasonic transducer in a test fixture that includes an ultrasonic target disposed therein at a known position;

manipulating the probe in the test fixture while operating the ultrasonic transducer until an output signal of the transducer indicates that the transducer is in alignment with the ultrasonic target;

measuring a position signal generated by the position sensor while the transducer is in alignment with the ultrasonic target, so as to determine an orientation of the probe in a frame of reference of the test fixture; and determining calibration data for the probe responsive to the orientation of the probe.

The calibration data typically include an alignment of the ultrasonic transducer with respect to an axis of the probe, and determining the calibration data includes determining the alignment. Alternatively or additionally, the calibration data include an alignment of the ultrasonic transducer with respect to the position sensor, and determining the calibration data includes determining the alignment.

In an embodiment, the probe includes a distal tip, the calibration data include a measure of a displacement of the ultrasonic transducer relative to the distal tip, and determining the calibration data includes determining the measure of displacement.

In an embodiment, determining the calibration data includes determining the calibration data for the probe responsive to the orientation of the probe and the known position of the ultrasonic target relative to the test fixture.

Manipulating the probe typically includes varying a rotational axis of the probe selected from the set consisting of: a roll of the probe, a yaw of the probe, and a pitch of the probe. For example, manipulating the probe may include rotating the probe about a long axis of the probe. Alternatively or additionally, manipulating the probe includes manipulating the probe in the test fixture while operating the ultrasonic transducer, so as to form an image of the ultrasonic target, until the output signal indicates that the transducer is in alignment with the ultrasonic target.

For some applications, manipulating the probe includes manipulating the probe manually, while for other applications manipulating the probe includes manipulating the probe in an automated manner.

In an embodiment, measuring the position signal includes generating at least two magnetic fields in the test fixture. Alternatively or additionally, the position sensor includes at least two coils, and measuring the position signal includes measuring a coil signal for each of the coils.

For some applications, measuring the position signal includes modifying a temperature of the probe. For example, modifying the temperature of the probe may include heating the probe or cooling the probe.

The probe typically includes a programmable microcircuit, and determining the calibration data includes recording the calibration data in the microcircuit. For example, recording the calibration data includes may include encrypting a calibration code.

The test fixture typically includes a clamp assembly, and placing the probe in the test fixture includes placing the probe in the clamp assembly. For example, the clamp fixture may be shaped to define a groove, and placing the probe in the test fixture includes placing the probe in the groove.

In an embodiment:

the test fixture includes at least two radiator coils fixed in known positions, placing the probe includes aligning the probe in a known orientation relative to the radiator coils, measuring the position signal includes activating the radiator coils so as to generate known magnetic fields in the test fixture, and measuring a position-sensor-calibration position signal generated by the position sensor, so as to determine a position-sensor orientation of the position sensor with respect to an axis of the probe, and determining the calibration data includes determining position-sensor calibration data for the probe responsive to the orientation of the position sensor.

In this case, for some applications, the probe includes a distal tip, and determining the position-sensor calibration data includes determining a measure of displacement of the position sensor relative to the distal tip.

Alternatively or additionally:

measuring the position signal includes measuring the position signal so as to determine an orientation of the ultrasonic transducer relative to the position sensor, and determining the calibration data for the probe includes determining an alignment of the ultrasonic transducer with respect to the axis of the probe, responsive to the orientation of the ultrasonic transducer relative to the position sensor, and responsive to the position-sensor orientation with respect to the axis of the probe.

Further alternatively or additionally, the position sensor includes at least two coils, and measuring the position-sensor-calibration position signal includes measuring a coil-calibration signal for each of the coils. In this case, determining the position-sensor calibration data for the probe may include calibrating a gain of each coil. Alternatively or additionally, determining the position-sensor calibration data for the probe includes determining, for each coil, a deviation of the coil from alignment with the axis of the probe.

There is further provided, in accordance with an embodiment of the present invention, a method for calibration, including:

placing a probe that includes an ultrasonic transducer in a test fixture that includes an ultrasonic target disposed therein at a known position;

manipulating the probe in the test fixture while operating the ultrasonic transducer until an output signal of the transducer indicates that the transducer is in alignment with the ultrasonic target;

mechanically measuring an orientation of the probe in a frame of reference of the test fixture, while the transducer is in alignment with the ultrasonic target; and determining calibration data for the probe responsive to the orientation of the probe.

There is still further provided, in accordance with an embodiment of the present invention, a method for calibration, including:

placing a probe that includes an ultrasonic transducer in a test fixture that includes an ultrasonic target disposed therein;

moving the ultrasonic target in the test fixture while operating the ultrasonic transducer until an output signal of the transducer indicates that the transducer is in alignment with the ultrasonic target;

measuring, while the transducer is in alignment with the ultrasonic target, a position of the ultrasonic target in a frame of reference of the test fixture, so as to determine an orientation of the probe in the frame of reference of the test fixture; and determining calibration data for the probe responsive to the orientation of the probe.

There is yet further provided, in accordance with an embodiment of the present invention, a method for calibration, including:

placing a probe that includes a position sensor and an imaging device in a test fixture, which includes an imaging target disposed therein at a known position;

manipulating the probe in the test fixture while operating the imaging device until an output signal of the imaging device indicates that the imaging device is in alignment with the imaging target;

measuring a position signal generated by the position sensor while the imaging device is in alignment with the imaging target, so as to determine an orientation of the probe in a frame of reference of the test fixture; and determining calibration data for the probe responsive to the orientation of the probe.

There is also provided, in accordance with an embodiment of the present invention, apparatus for calibrating a probe having a position sensor and an ultrasonic transducer, the apparatus including:

a test fixture, which includes an ultrasonic target disposed therein at a known position; and a computer, adapted to:

receive a position signal generated by the position sensor while the transducer is in alignment with the ultrasonic target, determine an orientation of the probe in a frame of reference of the test fixture, and determine calibration data for the probe responsive to the orientation of the probe.

For some applications, the calibration data include an alignment of the ultrasonic transducer with respect to an axis of the probe, and the computer is adapted to determine the alignment. Alternatively or additionally, the calibration data include an alignment of the ultrasonic transducer with respect to the position sensor, and the computer is adapted to determine the alignment.

In an embodiment, the probe includes a distal tip, the calibration data include a measure of a displacement of the ultrasonic transducer relative to the distal tip, and the computer is adapted to determine the measure of displacement.

Alternatively or additionally, the computer is adapted to determine the calibration data for the probe responsive to the orientation of the probe and the known position of the ultrasonic target relative to the test fixture.

In an embodiment, the ultrasonic target includes a bubble including an ultrasound-reflecting material.

The position sensor typically includes at least two coils, and the computer is adapted to receive the position signal responsive to current in the coils.

For some applications, the test fixture includes a heating element, adapted to heat or cool the probe.

The ultrasonic target is typically adapted to be movable within the test fixture.

For some applications, the probe includes a programmable microcircuit, and the computer is adapted to record the calibration data in the microcircuit. In this case, the computer may be adapted to encrypt a calibration code.

The test fixture typically includes a clamp assembly, adapted to hold the probe. The clamp assembly is typically adapted to allow an orientation of the probe to be varied on a rotational axis of the probe selected from the set consisting of: a roll of the probe, a yaw of the probe, and a pitch of the probe. Alternatively or additionally, the clamp assembly is shaped to define a groove, adapted to hold the probe. Further alternatively or additionally, the clamp assembly is adapted to manipulate the probe in an automated manner.

In an embodiment, the test fixture includes at least two radiator coils fixed in known positions. The test fixture typically includes three mutually-orthogonal pairs of parallel radiator coils. For some applications, the radiator coils are adapted to generate respective magnetic fields in the test fixture, and the computer is adapted to receive the position signal generated by the position sensor responsive to the magnetic fields.

In an embodiment, the computer is adapted to:

receive a position-sensor-calibration position signal generated by the position sensor while the probe is aligned in a known orientation relative to the radiator coils, determine a position-sensor orientation of the position sensor with respect to an axis of the probe, and determine position-sensor calibration data for the probe responsive to the orientation of the position sensor.

In this case, in an embodiment of the present invention, the probe includes a distal tip, the position-sensor calibration data include a measure of a displacement of the position sensor relative to the distal tip, and the computer is adapted to determine the measure of displacement.

Alternatively or additionally:

the calibration data for the probe include an alignment of the ultrasonic transducer with respect to the axis of the probe, and the computer is adapted to:

determine an orientation of the ultrasonic transducer relative to the position sensor, and determine the alignment of the ultrasonic transducer with respect to the axis of the probe, responsive to the orientation of the ultrasonic transducer relative to the position sensor, and responsive to the position-sensor orientation with respect to the axis of the probe.

In an embodiment, the position sensor includes at least two coils, and the computer is adapted to measure a coil-calibration signal for each of the coils. For example, the computer may be adapted to calibrate a gain of each coil. Alternatively or additionally, the computer is adapted to determine, for each coil, a deviation of the coil from alignment with the axis of the probe.

There is additionally provided, in accordance with an embodiment of the present invention, apparatus for calibrating a probe having an ultrasonic transducer, the apparatus including:

a test fixture, which includes an ultrasonic target disposed therein at a known position, and a measurement device, adapted to mechanically measure an orientation of the probe in a frame of reference of the test fixture, and to generate an orientation signal responsive to the measurement; and a computer, adapted to:

receive the orientation signal generated by the measurement device while the transducer is in alignment with the ultrasonic target, and determine calibration data for the probe responsive to the orientation signal.

There is still additionally provided, in accordance with an embodiment of the present invention, apparatus for calibrating a probe having a position sensor and an imaging device, the apparatus including:

a test fixture, which includes an imaging target disposed therein at a known position; and a computer, adapted to:

receive a position signal generated by the position sensor while the imaging device is in alignment with the imaging target, determine an orientation of the probe in a frame of reference of the test fixture, and determine calibration data for the probe responsive to the orientation of the probe.

The present invention will be more fully understood from the following detailed description of the preferred embodiments thereof, taken together with the drawings in which:

DETAILED DESCRIPTION OF PREFERRED EMBODIMENTS

Figure 1:
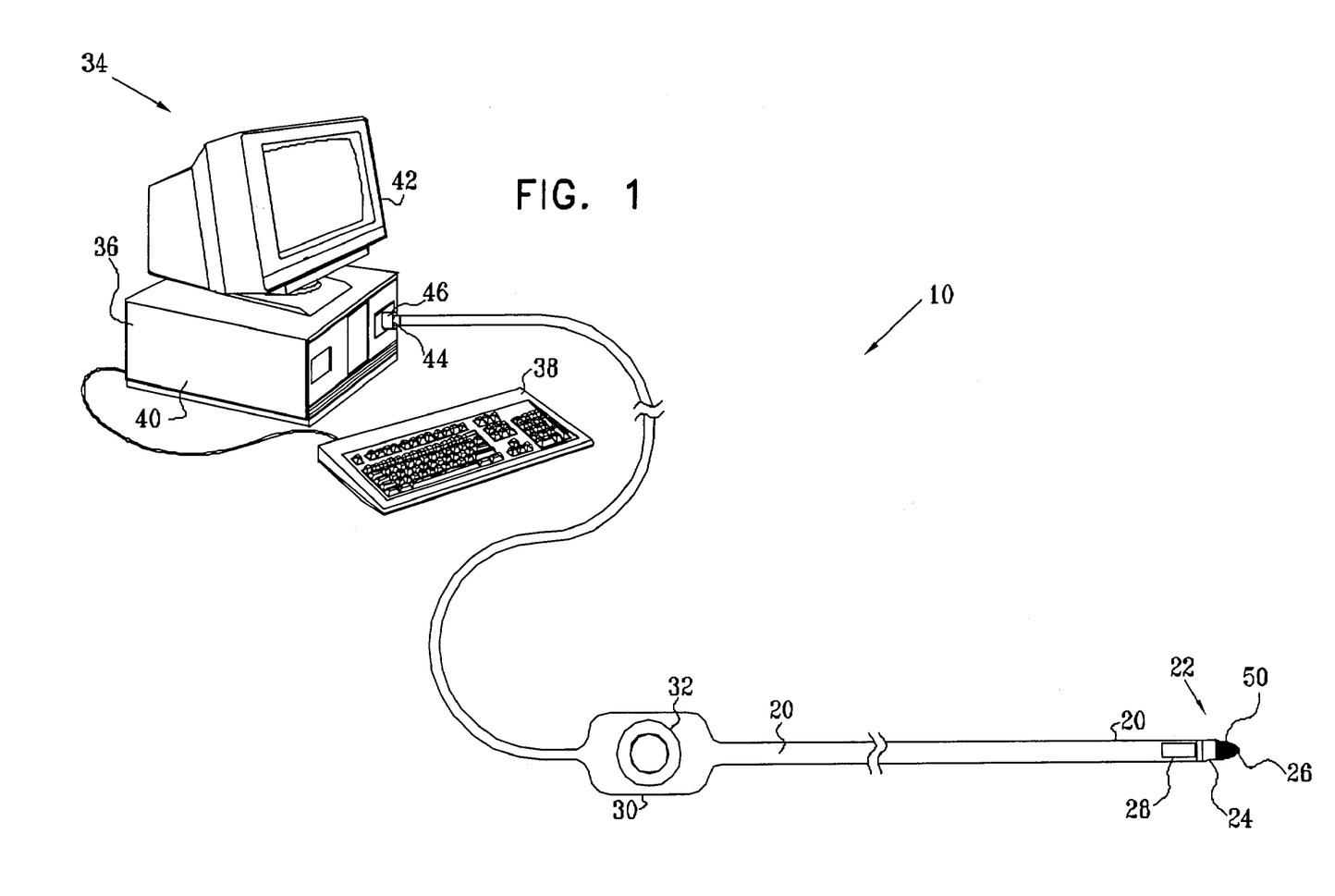
FIG. 1 is a simplified pictorial illustration of a system including a catheter, in accordance with a preferred embodiment of the present invention.

FIG. 1 is a simplified pictorial illustration of a catheter system 10 comprising an elongate probe, preferably a catheter 20, for insertion into the human body, in accordance with a preferred embodiment of the present invention. It is to be understood that although the following preferred embodiments are described with reference to a catheter, the present invention is equally applicable to other types of probes.

Catheter 20 preferably includes a handle 30 for operation of the catheter by a user, and controls 32 on handle 30 enable the user to steer a distal end 22 of the catheter in a desired direction, or to position and/or orient it as desired.

System 10 further comprises a console 34, which enables the user to observe and regulate the functions of catheter 20. Console 34 preferably includes a computer 36, a keyboard 38, signal processing circuits 40, which are typically inside the computer, and a display 42. Signal processing circuits 40 typically receive, amplify, filter and digitize signals from catheter 20, whereupon these digitized signals are received and used by computer 36 to compute the position and orientation of the catheter. Catheter 20 is coupled at its proximal end by a connector 44 to a mating receptacle 46 on console 34.

Figure 2:
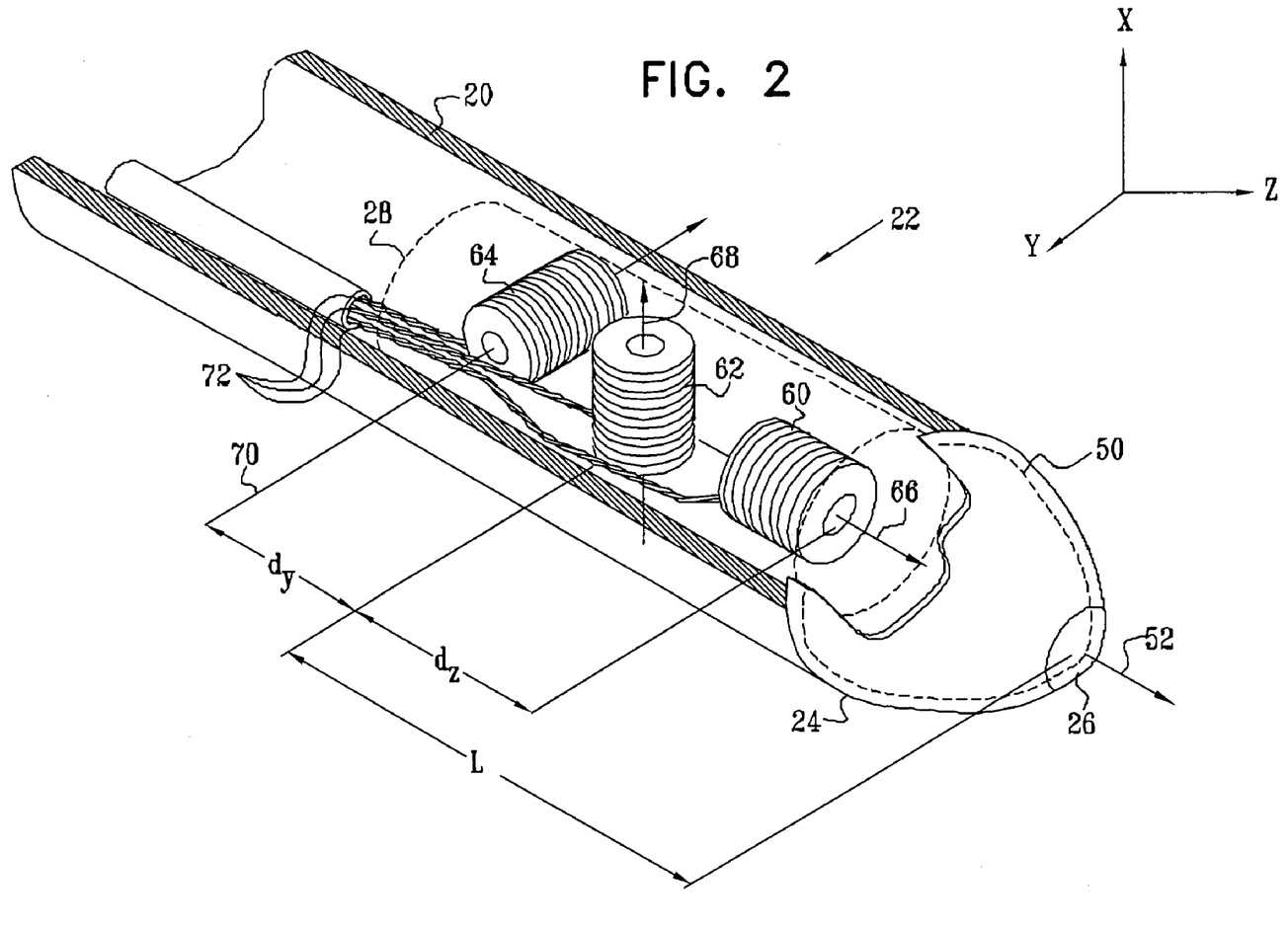
FIG. 2 is a schematic, pictorial illustration of the distal end of the catheter of FIG. 1, in accordance with a preferred embodiment of the present invention.

FIG. 2 is a schematic, pictorial illustration of distal end 22 of catheter 20, in accordance with a preferred embodiment of the present invention. Distal end 22 comprises a functional portion 24 for performing diagnostic and/or therapeutic functions, adjacent to a distal tip 26 of the catheter. Functional portion 24 comprises an ultrasound transducer 50, typically used for ultrasound imaging within a patient. Alternatively, ultrasound transducer 50 is used for other diagnostic purposes, such as Doppler measurements, or for therapeutic uses.

Distal end 22 of catheter 20 further includes a position sensing device 28 that generates signals used to determine the position and orientation of the catheter within the body. Position sensing device 28 is preferably adjacent to functional portion 24. There is preferably a fixed positional and orientational relationship between position sensing device 28 and portion 24.

Position sensing device 28 preferably comprises three non-concentric coils 60, 62 and 64, such as described in the above-cited European Patent 0 776 176 to Ben-Haim et al. This device enables continuous generation of six dimensions of position and orientation information. Coils 60, 62 and 64 have respective axes 66, 68 and 70 which preferably but not necessarily define orthogonal Cartesian axes Z, X and Y, respectively, as shown in FIG. 2, wherein the Z-axis is parallel to the long axis of catheter 20 and the X- and Y-axes define a plane perpendicular thereto. The coils each have a fixed position and orientation with respect to each other.

Although preferred embodiments of the present invention are described herein with reference to the position signal generating device shown in FIG. 2 and described above, it is to be understood that the inventive concepts of the present invention are similarly applicable to probes including other position sensing devices. For example, preferred embodiments of the present invention may comprise a single coil for generating position signals, or two or more such coils, which may be concentric or non-concentric. Other preferred embodiments of the present invention may comprise other types of position sensing devices, such as Hall effect devices.

As shown in FIG. 2, position sensing device 28 is located in catheter 20 at a distance L from distal tip 26, where L is here defined for convenience as the distance along the Z-axis from central axis 68 of coil 62 to tip 26. Respective axes 66 and 70 of coils 60 and 64 are displaced from axis 68 by respective distances $d_y$ and $d_z$.

Signal processing circuits 40 in console 34 receive signals carried by coil wires 72 from coils 60, 62, and 64, and convey them to computer 36, which computes the three-dimensional translational position of position sensing device 28 and the rotational orientation of axes 66, 68 and 70, relative to a fixed, external coordinate frame. The actual position and orientation of distal tip 26 are then computed by taking into account the distance L of tip 26 from the center of position sensing device 28, as defined by axis 68, and the orientation of axes 66, 68 and 70.

It has been found empirically that because of deviations in the process of manufacturing catheter 20, the distance L typically varies from one catheter to another, leading to errors in calculating the position of tip 26. Furthermore, axis 66 of coil 60 typically deviates from absolute alignment with the long axis of catheter 20, which passes through tip 26. Moreover, axes 68 and 70 of coils 62 and 64 respectively are typically not precisely orthogonal to axis 66 or to each other, thereby inducing additional errors in determination of position and orientation of the catheter. Additionally, axis 52 of ultrasound transducer 50 typically deviates from absolute alignment with the long axis of catheter 20, and from axis 66 of coil 60. Finally, variations in the respective gains of coils 60, 62 and 64 and in the distances $d_y$ and $d_z$ may cause additional errors in determination of position and orientation of the catheter.

Therefore, in preferred embodiments of the present invention, position sensing device 28 and ultrasound transducer 50 are calibrated before the catheter is inserted into a patient's body. Preferably this calibration is performed using one or more jigs, such as those shown, for example, in FIGS. 3A, 3B and 3C.

Figure 3A:
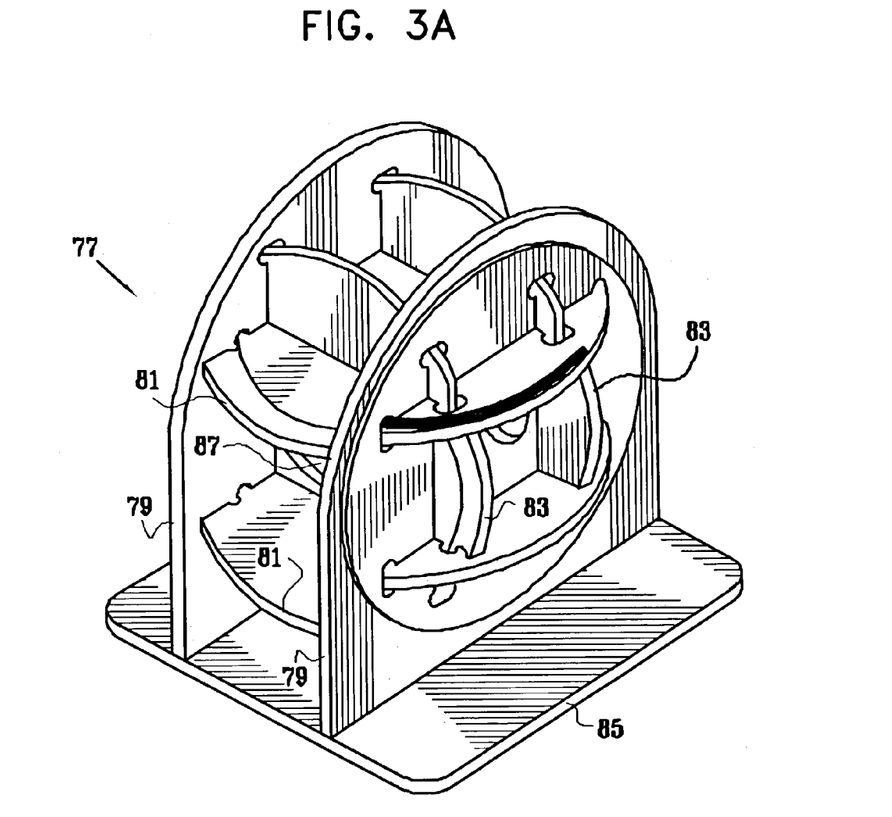
FIG. 3A is a perspective view of a jig useful in calibrating a catheter, in accordance with a preferred embodiment of the present invention.
Figure 3B:
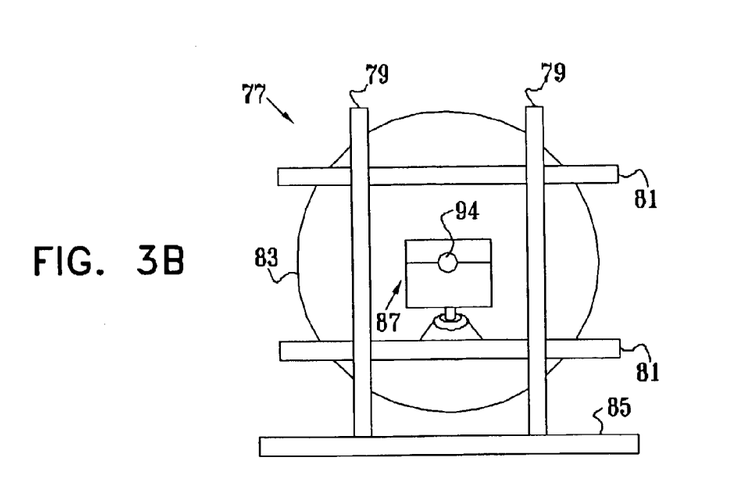
FIG. 3B is a schematic side view of the jig of FIG. 3A.
Figure 3C:
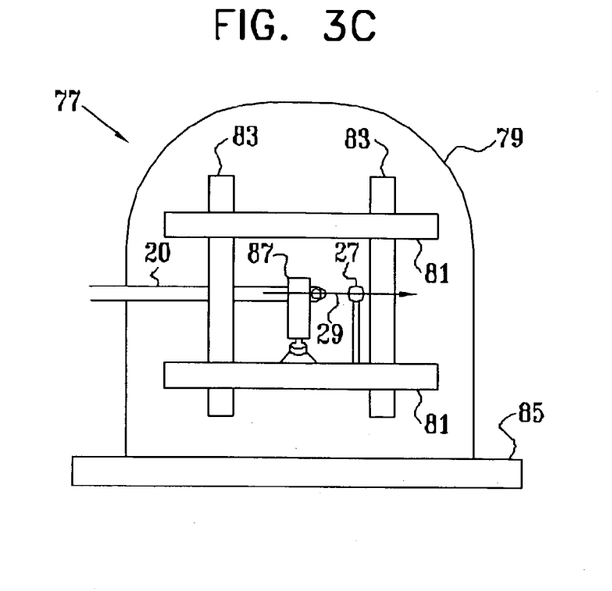
FIG. 3C is a further schematic side view of the jig of FIG. 3A, viewed from a side different from that in FIG. 3B.

FIGS. 3A, 3B and 3C show a preferred embodiment of a jig 77 for use in calibrating the gains and deviations from orthogonality of coils 60, 62 and 64, and for calibrating the ultrasound transducer's deviation from alignment with the long axis of catheter 20, and from axis 66 of coil 60. Jig 77 comprises three mutually-orthogonal pairs of parallel radiator coils 79, 81 and 83, mounted on a base 85. The radiator coils are coupled to radiator driver circuitry (not shown), which causes the radiator coils to generate magnetic fields. Each radiator coil pair generates a magnetic field that is substantially normal to the planes defined by the pair of coils, and is thus substantially orthogonal to fields generated by the other two radiator coil pairs.

The radiator coils are configured so as to generate predetermined, substantially uniform magnetic fields in a region adjacent to the center of the jig, i.e., in a region centrally located in between the three pairs of radiator coils. Preferably the driver circuitry is configured so that the amplitudes of the respective magnetic fields generated by the three radiator coil pairs are equal.

Figure 3D:
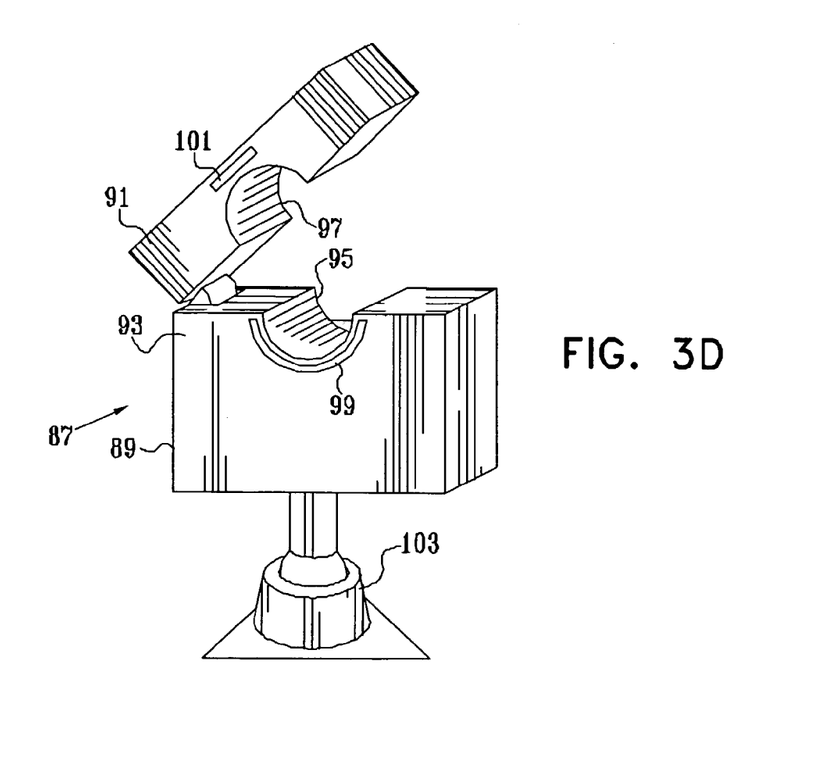
FIG. 3D is a perspective view of a catheter clamp for use in conjunction with the jig of FIG. 3A, in accordance with a preferred embodiment of the present invention.

As shown in FIG. 3B, jig 77 further comprises a catheter clamp assembly 87, which is located inside the jig and not seen in FIG. 3A. As shown in FIG. 3D, clamp assembly 87 comprises a clamp base 89. Clamp base 89 comprises a universal joint 103, which is able to pivot on the rotational axes of pitch and yaw with respect to the long axis of catheter 20. A base portion of universal joint 103 is typically fixed to a housing supporting one or more of radiator coils 79, 81 and 83 in a known position and orientation. Preferably clamp assembly 87 is constructed and configured in jig 77 so that a catheter held in the clamp assembly will be in the region of substantially uniform magnetic fields adjacent to the center of the jig, and so that the long axis of the catheter will be substantially normal to the planes defined by one of the pairs of parallel radiator coils (for example, coils 83 as shown in FIG. 3B). A clamp cover 91 is rotatably attached to base 89 by a hinge 93. Base 89 and cover 91 include respective semi-circular grooves 95 and 97, whose radii are substantially equal to the radius of catheter 20, and which together comprise circular groove 94 (shown in FIG. 3B).

As shown in FIG. 3C, jig 77 further comprises an ultrasound target 27 of known geometry, size, and material, fixed in a known position. Target 27, for example, may comprise a small "bubble" made of ultrasound-reflecting material. Target 27 may also be of different geometries and/or sizes.

Clamp assembly 89 preferably includes a heating element 99 and at least one temperature sensor 101, which are used to heat distal end 22 of catheter 20 to a temperature substantially equal to the temperature of the body into which the catheter is to be inserted, and to maintain the distal end at that temperature during calibration. As is known in the art, the response of coils 60, 62 and 64 to magnetic fields may change as a function of temperature. For example, when the coils are wound around ferrite cores, their inductance may change with temperature, which change can introduce errors into the calibration of position sensing device 28. Therefore, distal end 22 is typically heated to and maintained at a temperature of 37 degrees C. during calibration, although other temperatures may be chosen, for example when catheter 20 is to be used under conditions of hypothermia, such as are generally induced during open-heart surgery.

Although preferred embodiments of the present invention are described herein with reference to the jig shown in FIGS. 3A, 3B, and 3C and described above, it is to be understood that the inventive concepts of these embodiments of the present invention are similarly applicable to alternative jigs. Any jig that provides known, accurate magnetic field strengths, an ultrasound target with a known, fixed position, and means for securing catheter 20 in a known position, can be used for this purpose.

In a preferred embodiment of the present invention, to use jig 77 in calibrating position sensing device 28 with respect to catheter 20, the catheter is inserted in groove 95 with distal end 22 of the catheter pointing in the direction of target 27. Distal end 22 is preferably inserted into clamp assembly 87 so that it protrudes therefrom by a predetermined distance. The desired distance may be indicated, for example, by fiducial marks or other features (not shown) on the catheter's outer surface. The catheter is rotated about its long axis to a desired rotational orientation, wherein preferably the X, Y and Z catheter axes shown in FIG. 2 are substantially aligned with the magnetic field directions defined by radiator coil pairs 83, 79 and 81, respectively. Alternatively, in preferred embodiments of the present invention in which catheter 20 is rotationally symmetrical about its long axis, the rotational orientation is unimportant.

After catheter 20 has been inserted and aligned, as appropriate, in groove 95, cover 91 is then lowered to hold the catheter in place. In this manner the catheter is fixed in a known orientation relative to the magnetic fields generated by radiator coils 81, 83 and 85, and relative to target 27.

The respective gains and angular orientations of catheter coils 60, 62 and 64 are then calibrated by sequentially activating radiator coil pairs 79, 81 and 83 to generate predetermined, known magnetic fields, and measuring the amplitudes of the signals generated by the catheter coils.

First, to calibrate the gains of the coils, total amplitudes of the respective catheter coil signals are derived by summing the squares of the amplitudes of the signals generated by each of catheter coils 60, 62 and 64 in response to each of the coil pairs in turn. Since the magnetic fields in the vicinity of coils 60, 62 and 64 have equal and substantially uniform components along each of the coil axes 66, 68 and 70, the total signal amplitudes will be independent of the respective orientations and positions of coils 60, 62 and 64, and will depend only on the respective coil gains. Thus, the measured total signal amplitudes may be used to determine respective normalization factors for coils 60, 62 and 64, by dividing the measured amplitudes by expected standard values. Subsequently the amplitudes of signals received from these coils may be multiplied by the respective normalization factors in order to correct for gain variations.

Jig 77 is further used to calibrate the respective angular orientations of coils 60, 62 and 64 relative to catheter 20, so as to correct for deviations from orthogonality. The normalized amplitude of the signal generated by each of coils 60, 62 and 64 in response to each of the magnetic fields will be proportional to the cosine of the angle between the respective coil axis 66, 68 or 70, and the direction of the applied magnetic field. Three such angle cosines, corresponding to the directions of the three orthogonal magnetic fields applied by radiator coil pairs 79, 81 and 83, may thus be derived for each of catheter coils 60, 62 and 64. Since, as noted above, catheter 20 is held in clamp assembly 87 in such a manner that the X, Y and Z catheter axes are substantially aligned with the three orthogonal magnetic field directions, the orientations of the coils relative to the catheter axes may thus be determined.

In a preferred embodiment of the present invention, when the Z-axis magnetic field is activated, corresponding in this case to radiator coil pair 83, a normalized amplitude of the signal received from coil 60, $S_{60}(Z)$, is received and measured. The X- and Y-axis fields are similarly activated, and corresponding normalized signals $S_{60}(X)$ and $S_{60}(Y)$ are received. $S_{60}(X)$, $S_{60}(Y)$ and $S_{60}(Z)$ are used to calculate coil angle calibration factors for coil 60, which are thereafter recorded in catheter 20 and used in determining the catheter's position and orientation. A similar procedure is used to calibrate coils 62 and 64.

Although the magnetic fields generated by coil pairs 79, 81 and 83 are substantially orthogonal and of equal amplitudes, imprecise winding of the coil pairs may cause small deviations from orthogonality and equality. These deviations, if not corrected for, may cause errors in the calibration of catheter 20. Therefore, in a preferred embodiment of the present invention, a master coil (not shown) is used to calibrate jig 77, preferably as described in the above-cited U.S. Pat. No. 6,266,551 to Osadchy et al. When catheter 20 is placed in jig 77 for calibration of the catheter, the signals received from coils 60, 62 and 64 are preferably first corrected to account for the calibration factors of coil pairs 79, 81 and 83, and, subsequently, the gain normalization and angle calibration factors of the catheter described hereinabove are determined.

In a preferred embodiment of the present invention, jig 77 is further used to calibrate the angular orientation of ultrasound transducer 50 relative to position sensing device 28 and to catheter 20. Ultrasound transducer 50 emits ultrasonic radiation and generates an output signal responsive to the radiation reflected back from target 27. The roll, yaw, and/or pitch of the angular orientation of distal end 22 of catheter 20 are varied until the output signal indicates that ultrasound transducer 50 is in a suitable alignment with target 27. This alignment is preferably performed by forming an image of the target, or, alternatively, by using other methods that will be apparent to those skilled in the art, having read the disclosure of the present patent application. Methods of honing in on the target will also be apparent to those skilled in the art. The manipulation of the angular orientation of the catheter can be performed manually or by automated means.

The angles of the yaw and pitch of distal end 22 relative to fixed and known axis 29 extending from the center of groove 94 (FIG. 3B) to target 27 are measured. This measurement is preferably performed with position sensing device 28 by comparing the device's current orientation, in alignment with the target, with its orientation prior to aligning the ultrasound transducer with the target. Alternatively, the measurement is performed using mechanical means known in the art. The distances between the distal end of ultrasound transducer 50 and the center of groove 94, between the distal end of ultrasound transducer 50 and target 27, and between the distal end of ultrasound transducer 50 and position sensing device 28 are known, so using the measured angles and these distances, the exact orientation of axis 52 of ultrasound transducer 50 relative to position sensing device 28, and the exact orientation of axis 52 relative to the long axis of catheter 20 are readily calculated. (Any change in the distance between tip 26 and target 27 caused by the pivoting of universal joint 103 can readily be calculated and compensated for.)

For some applications, in which deviations in the process of manufacturing catheter 20 result in meaningful variations of the displacement of ultrasound transducer 50 relative to catheter tip 26, this displacement is calibrated. Preferably, methods described hereinabove are used to perform this calibration. In a preferred embodiment of the present invention, the respective angular orientations of coils 60, 62 and 64 relative to ultrasound transducer 50 are directly calculated. In this embodiment, the intermediary step of calibrating the orientations of the coils relative to catheter 20 is not performed. This calibration technique is particularly advantageous for applications in which catheter 20 does not comprise diagnostic or therapeutic elements other than the ultrasound transducer, because in such applications there is generally no need to know the precise orientation of the catheter during a procedure.

For some applications, ultrasound transducer 50 is disposed perpendicular to the long axis of catheter 20, rather than parallel to this long axis. Calibration techniques described herein are modified appropriately.

In a preferred embodiment of the present invention, catheter 20 is held in a fixed position in the jig during calibration, and ultrasound target 27 is moved in the jig until ultrasound transducer 50 is brought into alignment with the target.

In a preferred embodiment of the present invention, the displacements of coils 60, 62 and 64 relative to catheter tip 26 are calibrated. This is preferably performed by using a jig (not shown) and methods for this purpose, such as those described in the above-cited U.S. Pat. No. 6,266,551 to Osadchy et al.

In a preferred embodiment of the present invention, the calibration corrections that are determined in accordance with the methods described hereinabove are thereafter stored electronically in a memory device, which is preferably incorporated in catheter 20. When the catheter is coupled to console 34, this memory device is accessible to computer 36 in the console. Apparatus and methods for enabling the use of such a memory device that are described in the above-cited U.S. Pat. No. 6,266,551 to Osadchy et al. may be used, or, alternatively, other apparatus and methods known in the art may be used.

Although embodiments of the present invention have been described with respect to an ultrasound transducer, it is to be understood that apparatus and methods described herein are equally applicable to devices on a catheter that perform other imaging modalities. Additionally, although embodiments of the present invention have been described to include the steps of calibrating the gains of the coils, calibrating the respective angular orientations of the coils relative to the catheter, and calibrating the displacements of the coils relative to the catheter tip, these steps can optionally be omitted. Furthermore, although embodiments of the present invention have been described with respect to coil-based position sensors, the techniques described herein are similarly applicable to position sensors that are not coil-based.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method for calibration, comprising:
placing a probe that includes a distal tip, a position sensor and an ultrasonic transducer in a test fixture that includes an ultrasonic target disposed therein at a known position;
manipulating the probe in the test fixture while operating the ultrasonic transducer until an output signal of the transducer indicates that the transducer is in alignment with the ultrasonic target;
measuring a position signal generated by the position sensor while the transducer is in alignment with the ultrasonic target, so as to determine an orientation of the probe in a frame of reference of the test fixture;
measuring a displacement of the ultrasonic transducer relative to the distal tip and;
determining calibration data for the probe responsive to the orientation of the probe and determining the measure of displacement.

2. A method according to claim 1, wherein the calibration data include an alignment of the ultrasonic transducer with respect to an axis of the probe, and wherein determining the calibration data comprises determining the alignment.

3. A method according to claim 1, wherein the calibration data include an alignment of the ultrasonic transducer with respect to the position sensor, and wherein determining the calibration data comprises determining the alignment.

4. A method according to claim 1, wherein the calibration data include an alignment of the ultrasonic transducer with respect to the position sensor and an alignment of the ultrasound transducer with respect to an axis of the probe, and wherein determining the calibration data comprises determining the alignments.

5. A method according to claim 1, wherein determining the calibration data comprises determining the calibration data for the probe responsive to the orientation of the probe and the known position of the ultrasonic target relative to the test fixture.

6. A method according to claim 1, wherein manipulating the probe comprises varying a rotational axis of the probe selected from the set consisting of: a roll of the probe, a yaw of the probe, and a pitch of the probe.

7. A method according to claim 1, wherein manipulating the probe comprises manipulating the probe in the test fixture while operating the ultrasonic transducer, so as to form an image of the ultrasonic target, until the output signal indicates that the transducer is in alignment with the ultrasonic target.

8. A method according to claim 1, wherein manipulating the probe comprises manipulating the probe manually.

9. A method according to claim 1, wherein manipulating the probe comprises manipulating the probe in an automated manner.

10. A method according to claim 1, wherein measuring the position signal comprises generating at least two magnetic fields in the test fixture.

11. A method according to claim 1, wherein the position sensor includes at least two coils, and wherein measuring the position signal comprises measuring a coil signal for each of the coils.

12. A method according to claim 1, wherein manipulating the probe comprises rotating the probe about a long axis of the probe.

13. A method according to claim 1, wherein measuring the position signal comprises modifying a temperature of the probe.

14. A method according to claim 13, wherein modifying the temperature of the probe comprises heating the probe.

15. A method according to claim 13, wherein modifying the temperature of the probe comprises cooling the probe.

16. A method according to claim 1, wherein the probe includes a programmable microcircuit, and wherein determining the calibration data comprises recording the calibration data in the microcircuit.

17. A method according to claim 16, wherein recording the calibration data comprises encrypting a calibration code.

18. A method according to claim 1, wherein the test fixture includes a clamp assembly, and wherein placing the probe in the test fixture comprises placing the probe in the clamp assembly.

19. A method according to claim 18, wherein the clamp fixture is shaped to define a groove, and wherein placing the probe in the test fixture comprises placing the probe in the groove.

20. A method according to claim 1,
wherein the test fixture includes at least two radiator coils fixed in known positions,
wherein placing the probe comprises aligning the probe in a known orientation relative to the radiator coils,
wherein measuring the position signal comprises activating the radiator coils so as to generate known magnetic fields in the test fixture, and measuring a position-sensor-calibration position signal generated by the position sensor, so as to determine a position-sensor orientation of the position sensor with respect to an axis of the probe, and
wherein determining the calibration data comprises determining position-sensor calibration data for the probe responsive to the orientation of the position sensor.

21. A method according to claim 20, wherein the probe includes a distal tip, and wherein determining the position-sensor calibration data comprises determining a measure of displacement of the position sensor relative to the distal tip.

22. A method according to claim 20,
wherein measuring the position signal comprises measuring the position signal so as to determine an orientation of the ultrasonic transducer relative to the position sensor, and
wherein determining the calibration data for the probe comprises determining an alignment of the ultrasonic transducer with respect to the axis of the probe, responsive to the orientation of the ultrasonic transducer relative to the position sensor, and responsive to the position-sensor orientation with respect to the axis of the probe.

23. A method according to claim 20, wherein the position sensor includes at least two coils, and wherein measuring the position-sensor-calibration position signal comprises measuring a coil-calibration signal for each of the coils.

24. A method according to claim 23, wherein determining the position-sensor calibration data for the probe comprises calibrating a gain of each coil.

25. A method according to claim 23, wherein determining the position-sensor calibration data for the probe comprises determining, for each coil, a deviation of the coil from alignment with the axis of the probe.

26. A method for calibration, comprising:
placing a probe that includes a distal tip, a position sensor and an imaging device in a test fixture, which comprises an imaging target disposed therein at a known position;
manipulating the probe in the test fixture while operating the imaging device until an output signal of the imaging device indicates that the imaging device is in alignment with the imaging target;
measuring a position signal generated by the position sensor while the imaging device is in alignment with the imaging target, so as to determine an orientation of the probe in a frame of reference of the test fixture;
measuring a displacement of the imaging device relative to the distal tip;
determining calibration data for the probe responsive to the orientation of the probe and determining the measure of displacement.

27. Apparatus for calibrating a probe having a distal tip, a position sensor and an ultrasonic transducer, the apparatus comprising:
a test fixture, which comprises an ultrasonic target disposed therein at a known position; and
a computer, adapted to:
receive a position signal generated by the position sensor while the transducer is in alignment with the ultrasonic target,
determine an orientation of the probe in a frame of reference of the test fixture,
measuring a displacement of the ultrasonic transducer relative to the distal tip;
determine calibration data for the probe responsive to the orientation of the probe; and
determine the measure of displacement.

28. Apparatus according to claim 27, wherein the calibration data include an alignment of the ultrasonic transducer with respect to an axis of the probe, and wherein the computer is adapted to determine the alignment.

29. Apparatus according to claim 27, wherein the calibration data include an alignment of the ultrasonic transducer with respect to the position sensor, and wherein the computer is adapted to determine the alignment.

30. Apparatus according to claim 27, wherein the calibration data include an alignment of the ultrasonic transducer with respect to the position sensor and an alignment of the ultrasound transducer with respect to an axis of the probe, and wherein the computer is adapted to determine the alignments.

31. Apparatus according to claim 27, wherein the computer is adapted to determine the calibration data for the probe responsive to the orientation of the probe and the known position of the ultrasonic target relative to the test fixture.

32. Apparatus according to claim 27, wherein the ultrasonic target comprises a bubble comprising an ultrasound-reflecting material.

33. Apparatus according to claim 27, wherein the position sensor includes at least two coils, and wherein the computer is adapted to receive the position signal responsive to current in the coils.

34. Apparatus according to claim 27, wherein the test fixture comprises a heating element, adapted to heat the probe.

35. Apparatus according to claim 27, wherein the ultrasonic target is adapted to be movable within the test fixture.

36. Apparatus according to claim 27, wherein the probe includes a programmable microcircuit, and wherein the computer is adapted to record the calibration data in the microcircuit.

37. Apparatus according to claim 36, wherein the computer is adapted to encrypt a calibration code.

38. Apparatus according to claim 27, wherein the test fixture comprises a clamp assembly, adapted to hold the probe.

39. Apparatus according to claim 38, wherein the clamp assembly is adapted to allow an orientation of the probe to be varied on a rotational axis of the probe selected from the set consisting of: a roll of the probe, a yaw of the probe, and a pitch of the probe.

40. Apparatus according to claim 38, wherein the clamp assembly is shaped to define a groove, adapted to hold the probe.

41. Apparatus according to claim 38, wherein the clamp assembly is adapted to manipulate the probe in an automated manner.

42. Apparatus according to claim 27, wherein the test fixture comprises at least two radiator coils fixed in known positions.

43. Apparatus according to claim 42, wherein the test fixture comprises three mutually-orthogonal pairs of parallel radiator coils.

44. Apparatus according to claim 42, wherein the radiator coils are adapted to generate respective magnetic fields in the test fixture, and wherein the computer is adapted to receive the position signal generated by the position sensor responsive to the magnetic fields.

45. Apparatus according to claim 42, wherein the computer is adapted to:
receive a position-sensor-calibration position signal generated by the position sensor while the probe is aligned in a known orientation relative to the radiator coils,
determine a position-sensor orientation of the position sensor with respect to an axis of the probe, and
determine position-sensor calibration data for the probe responsive to the orientation of the position sensor.

46. Apparatus according to claim 45, wherein the probe includes a distal tip, wherein the position-sensor calibration data include a measure of a displacement of the position sensor relative to the distal tip, and wherein the computer is adapted to determine the measure of displacement.

47. Apparatus according to claim 45,
wherein the calibration data for the probe include an alignment of the ultrasonic transducer with respect to the axis of the probe, and
wherein the computer is adapted to:
determine an orientation of the ultrasonic transducer relative to the position sensor, and
determine the alignment of the ultrasonic transducer with respect to the axis of the probe, responsive to the orientation of the ultrasonic transducer relative to the position sensor, and responsive to the position-sensor orientation with respect to the axis of the probe.

48. Apparatus according to claim 45, wherein the position sensor comprises at least two coils, and wherein the computer is adapted to measure a coil-calibration signal for each of the coils.

49. Apparatus according to claim 48, wherein the computer is adapted to calibrate a gain of each coil.

50. Apparatus according to claim 48, wherein the computer is adapted to determine, for each coil, a deviation of the coil from alignment with the axis of the probe.

51. Apparatus for calibrating a probe having a distal tip, a position sensor and an imaging device, the apparatus comprising:
a test fixture, which comprises an imaging target disposed therein at a known position; and
a computer, adapted to:
receive a position signal generated by the position sensor while the imaging device is in alignment with the imaging target,
determine an orientation of the probe in a frame of reference of the test fixture,
determine a displacement of the imaging device relative to the distal tip;
determine calibration data for the probe responsive to the orientation of the probe; and
determine the measurement of displacement.

* * * * *